United States Patent [19]

Syverson

[11] Patent Number: 5,612,045

[45] Date of Patent: Mar. 18, 1997

[54] INHIBITION OF EXOPROTEIN IN ABSORBENT ARTICLE

[75] Inventor: Rae E. Syverson, Fond du Lac, Wis.

[73] Assignee: Kimberly-Clark Corporation, Neenah, Wis.

[21] Appl. No.: 487,950

[22] Filed: Jun. 7, 1995

[51] Int. Cl.⁶ .................................................. A01N 25/34
[52] U.S. Cl. ........................ 424/402; 424/404; 604/360
[58] Field of Search ................................ 424/402, 404; 604/360

[56] References Cited

U.S. PATENT DOCUMENTS

| | | | |
|---|---|---|---|
| 2,154,449 | 4/1939 | Hoffman et al. | 99/90 |
| 2,190,714 | 2/1940 | Hoffman et al. | 99/224 |
| 2,290,173 | 8/1940 | Epstein et al. | 167/22 |
| 2,290,174 | 10/1940 | Epstein et al. | 167/22 |
| 2,321,594 | 6/1943 | Harris | 260/404 |
| 2,340,311 | 2/1944 | Donovan | 128/285 |
| 2,440,141 | 4/1948 | Donovan | 128/285 |
| 2,466,663 | 4/1949 | Russ et al. | 167/58 |
| 2,467,884 | 4/1949 | Elias | 167/58 |
| 2,623,841 | 12/1952 | Taub | 167/58 |
| 2,854,978 | 10/1958 | Millman et al. | 128/285 |
| 3,091,241 | 5/1963 | Kellett | 128/270 |
| 3,172,817 | 3/1965 | Leupold et al. | 167/90 |
| 3,331,742 | 7/1967 | Babayan | 167/82 |
| 3,490,454 | 1/1970 | Goldfarb et al. | 128/285 |
| 3,629,454 | 12/1971 | Barr et al. | 424/320 |
| 3,639,561 | 2/1972 | Gordon et al. | 424/28 |
| 3,652,764 | 3/1972 | Lamberti et al. | 424/235 |
| 3,994,298 | 11/1976 | Des Marais | 128/285 |
| 4,002,775 | 1/1977 | Kabara | 426/532 |
| 4,046,914 | 9/1977 | Hallgren et al. | 424/312 |
| 4,067,961 | 1/1978 | Laughlin | 424/15 |
| 4,273,118 | 6/1981 | Smith | 128/156 |
| 4,286,596 | 9/1981 | Rubinstein | 128/270 |
| 4,289,824 | 9/1981 | Smith | 428/288 |
| 4,300,561 | 11/1981 | Kaczmarzyk et al. | 128/285 |
| 4,343,788 | 8/1982 | Mustacich et al. | 424/78 |
| 4,343,798 | 8/1982 | Fawzi | 424/240 |
| 4,377,167 | 3/1983 | Kaczmarzyk et al. | 128/285 |
| 4,385,632 | 5/1983 | Odelhog | 604/360 |
| 4,392,848 | 7/1983 | Lucas et al. | 604/53 |
| 4,405,323 | 9/1983 | Auerbach | 604/285 |
| 4,406,884 | 9/1983 | Fawzi et al. | 424/81 |
| 4,410,442 | 10/1983 | Lucas et al. | 252/107 |
| 4,430,381 | 2/1984 | Harvey et al. | 428/284 |
| 4,431,427 | 2/1984 | Lefren et al. | 604/285 |
| 4,479,795 | 10/1984 | Mustacich et al. | 604/53 |
| 4,489,097 | 12/1984 | Stone | 424/318 |
| 4,585,792 | 4/1986 | Jacob et al. | 514/474 |
| 4,661,101 | 4/1987 | Sustmann | 604/360 |
| 4,675,014 | 6/1987 | Sustmann et al. | 604/375 |
| 4,722,937 | 2/1988 | Jacob et al. | 514/474 |
| 4,752,617 | 6/1988 | Kern | 514/547 |
| 4,959,341 | 9/1990 | Wallach | 502/404 |
| 5,068,064 | 11/1991 | Proietto et al. | 260/404.5 |
| 5,080,902 | 1/1992 | Allermark et al. | 424/430 |
| 5,201,326 | 4/1993 | Kubicki et al. | 128/832 |
| 5,208,257 | 5/1993 | Kabara | 514/552 |
| 5,213,802 | 5/1993 | Masten | 424/439 |
| 5,389,374 | 2/1995 | Brown-Skrobot | 424/431 |

FOREIGN PATENT DOCUMENTS

| | | |
|---|---|---|
| 0395099A2 | 10/1990 | European Pat. Off. . |
| 0405993A3 | 1/1991 | European Pat. Off. . |
| 0483835A1 | 5/1992 | European Pat. Off. . |
| 0483812A1 | 5/1992 | European Pat. Off. . |
| 0510619A1 | 10/1992 | European Pat. Off. . |
| 1307930 | 9/1962 | France . |
| 3309530C1 | 10/1984 | Germany . |
| 63-309604 | 12/1988 | Japan . |

OTHER PUBLICATIONS

Article Entitled "A Rapid, Sensitive Method for Detection of Alkaline Phosphatase–Conjugated Anti–Antibody of Western Blots" authored by blake, Johnston, Russell–Jones and Gotschlich Analytical Biochemistry 136, 175–179 (1984).

Article Entitled "Effect of Glycerol Monolaurate on Bacterial Growth and Toxin Production" authored by Schlievert, Deringer, Kim, Projan and Novick, Agents and Chemotherapy, Mar. 1992 (pp 626–631).

Article "Fatty Acids and Derivatives as Antimicrobial Agents" authored by Kabara (pp. 1–14).

Article "Production of Toxic Shock Syndrome Toxin 1 By *Staphylococcus aureus* as Determined By Tampon Disk–Membrane–Agar Method" Authored by Robbins, Reisier, Hehl and Bergdoll, Journal of Clinical Microbiology, Aug. 1987 (pp. 1446–1449).

Article "Toxic Shock Syndrome *Staphylococcus aureaus*: Effect of Tampons on Toxic Shock Syndrome Toxin 1 Production" Authored by Schleivert, Blomster and Kelly (pp. 666–671).

Article "fatty Acids and Derivatives as Antimicrobial Agents" Authored by Kabara, Swieczkowski Conley and Truant. Antimicrobial Agents and Chemotherapy, Jul. 1972, pp. 23–28.

Article "Magnesium, *Staphylococcus aureus* and Toxic Shock Syndrome" Authored by Kaas Magnesium 1988:7:315–319.

"The Effect of Glycerol Monolaurate on Growth of, and Production of Toxic Shock Syndrome Toxin 1 and Lipase by *Staphylococcus aureus*" Authored by Holland, Taylor and Farrell (pp. 41–55).

(List continued on next page.)

Primary Examiner—Jyothsna Venkat
Attorney, Agent, or Firm—Mark L. Davis

[57] ABSTRACT

Absorbent articles, such as catamenial tampons, for absorbing body fluids are disclosed which include an effective amount of a compound to substantially inhibit the production of exotoxins by Gram positive bacteria. The compound is one or more ether compounds having the general formula:

$R_1$—O—$R_2$ wherein $R_1$ is a straight or branched chain alkyl group having from 8 to 18 carbon atoms, and $R_2$ is selected from an alcohol, a polyalkoxylated sulfate salt and a polyalkoxylated sulfosuccinate salt.

24 Claims, No Drawings

OTHER PUBLICATIONS

Article "Toxin and Enzyme Characterization of *Staphylococcus aureus* Isolates From Patients With and Without Toxic Shock Syndrome" Authored by Schlievert et al. Annals of Internal Medicine, 1982:96 (Part 2):937–940.

"Detection and Quantitation of Toxic Shock Syndrome Toxin 1 in Vitro and In Vivo by Noncompetitive Enzyme–Linked Immunosorbent Assay" Authored by Rosten et al., Journal of Clinical Microbiology, Feb. 1987; pp. 327–332.

Article "Sequential Vaginal Cultures from Normal Young Women" Authored by Sautter et al. Journal of Clinical Microbiology, May 1980, pp. 479–484.

Article "Emerging Role of Lactobacilli in the Control and Maintenance of the Vaginal Bacterial Microflora" Authored by Redondo–Lopez et al., Reviews of Infectious Diseases—vol. 12, No. 5 pp. 856–872.

Article "Nasal and Vaginal *Staphylococcus aureus* in Young Women: Quantitive Studies" Annals of Internal Medicine, 1982:96 (Part 2):951–953.

Article "Methods for Quantitative and Qualitative Evaluation of Vaginal Microflora during During Menstruation" Authored by Onderdonk, Zamarchi, Walsh, Mellor, Munoz and Kass, Applied and Environmental Microbiology, Feb. 1986, pp. 333–339.

Article "The Vaginal Ecosystem," American Journal of Obstetrics and gynecology, vol. 165, No. 4, Part 2, Oct., 1991.

Article "Vaginal Flora in Health and Disease" Authored by Bryan Larsen, Clinical Obstetrics Gynecology, vol. 36, No. 1, Mar. 1993. 1

Article "Recovery of *Staphylococcus aureus* from Multiple Body Sites in Menstruating Women" Authored by Lansdell et al. Journal of Clinical Microbiology, Sep. 1984, pp. 307–310.

Article "Control of the Microbial Flora of the Vagina by $H_2O_2$–Generating Lactobacilli" Authored By Klebanoff et al., Dept. of Medicine of Obstetrics and Gynecology, The Journal of Infectious Diseases 1991:164:94–100.

Article "Quantitative Bacteriology of the Vaginal Flora" Authored by Bartlett et al., The Journal of Infectious Diseases, vol. 136, No. 2.

INHIBITION OF EXOPROTEIN IN ABSORBENT ARTICLE

FIELD OF THE INVENTION

The present invention relates to the inhibition of exoprotein in an absorbent article, such as vaginal tampons and sanitary napkins. More particularly, the invention relates to the incorporation of ether compositions into such absorbent articles and these compounds effects on Gram positive bacteria.

BACKGROUND OF THE INVENTION

Disposable absorbent devices for the absorption of human exudates are widely used. These disposable devices typically have a compressed mass of absorbent formed into the desired shape, which is typically dictated by the intended consumer use. In the area of a menstrual tampon, the device is intended to be inserted in a body cavity for absorption of the body fluids generally discharged during a woman's menstrual period.

There exists in the female body a complex process which maintains the vagina and physiologically related areas in a healthy state. In a female between the age of menarche and menopause, the normal vagina provides an ecosystem for a variety of microorganisms. Bacteria are the predominant type of microorganism present in the vagina; most women harbor about $10^9$ bacteria per gram of vaginal exudate. The bacterial flora of the vagina is comprised of both aerobic and anaerobic bacteria. The more commonly isolated bacteria are Lactobacillus species, corynebacteria, *Gardnerella vaginalis*, Staphylococcus species, Peptococcus species, aerobic and anaerobic Streptococcal species, and Bacteroides species. Other microorganisms that have been isolated from the vagina on occasion include yeast (*Candida albicans*), protozoa (*Trichomonas vaginalis*), mycoplasma (*Mycoplasma hominis*), chlamydia (*Chlamydia trachomatis*), and viruses (*Herpes simplex*). These latter organisms are generally associated with vaginitis or venereal disease, although they may be present in low numbers without causing symptoms.

Physiological, social and idiosyncratic factors affect the quantity and species of bacteria present in the vagina. Physiological factors include age, days of the menstrual cycle, and pregnancy. For example, vaginal flora present in the vagina throughout the menstrual cycle can include lactobacilli, corynebacterium, ureaplasma, and mycoplasma. Social and idiosyncratic factors include method of birth control, sexual practices, systemic disease (e.g. diabetes), and medication.

Bacterial proteins and metabolic products produced in the vagina can affect other microorganisms and the human host. For example, the vagina between menstrual periods is mildly acidic having a pH ranging from about 3.8 to about 4.5. This pH range is generally considered the most favorable condition for the maintenance of normal flora. At that pH, the vagina normally harbors the numerous species of microorganisms in a balanced ecology, playing a beneficial role in providing protection and resistance to infection and makes the vagina inhospitable to some species of bacteria such as *Staphylococcus aureus* (S. aureus). The low pH is a consequence of the growth of lactobacilli and their production of acidic products. Microorganisms in the vagina can also produce antimicrobial compounds such as hydrogen peroxide and bactericides directed at other bacterial species. One example is the lactocins, bacteriocin-like products of lactobacilli directed against other species of lactobacilli.

Some microbial products may affect the human host. For example, S. aureus can produce and excrete into its environment a variety of exoproteins including enterotoxins, Toxic Shock Syndrome Toxin-1 (TSST-1), and enzymes such as proteases and lipase.

S. aureus is found in the vagina of approximately 16% of healthy women of menstrual age. Approximately 25% of the S. aureus isolated from the vagina are capable of producing TSST-1. TSST-1 and some of the staphylococcal enterotoxins have been identified as causing Toxic Shock Syndrome (TSS) in humans.

Symptoms of TSS generally include fever, diarrhea, vomiting and a rash followed by a rapid drop in blood pressure. Systemic vital organ failure occurs in approximately 6% of those who contact the disease. S. aureus does not initiate TSS as a result of the invasion of the microorganism into the vaginal cavity. Instead as S. aureus grows and multiplies, it can produce Toxic Shock Syndrome Toxin 1 (TSST-1; synonyms: pyrogenic exotoxin C and enterotoxin F). Only after entering the bloodstream does the TSST-1 toxin act systemically and produce the symptoms attributed to Toxic Shock Syndrome.

Menstrual fluid has a pH of approximately 7.3. During menses, the pH of the vagina moves toward neutral and can become slightly alkaline. This change permits microorganisms whose growth is inhibited by an acidic environment the opportunity to proliferate. For example, S. aureus is more frequently isolated from vaginal swabs during menstruation than from swabs collected between menstrual periods.

There have been numerous attempts to reduce or eliminate pathogenic microorganisms and menstrually occurring TSS by incorporating into a tampon pledget one or more biostatic, biocidial, and/or detoxifying compounds. For example, L-ascorbic acid has been applied to a menstrual tampon to detoxify toxin found in the vagina of the human female during menstruation.

Incorporating glyceryl triacetate into a tampon pledget has been suggested. Glyceryl triacetate is readily broken down into glycerol and acetic acid by the enzymatic action of esterase. Esterase is present in the vaginal epithelium and in menstrual fluid. The enzymatic action of the esterase is in turn controlled by the pH of the environment, being more active when the pH is on the alkaline side. Since the pH of the vagina moves toward the alkaline side during menstruation, the enzymatic activity of the esterase automatically increases and attacks the glyceryl triacetate. This releases acetic acid rapidly, which has the potential to reduce the pH and enzymatic activity of the esterase. However, menstrual fluid is well buffered and the acetic acid is ineffective at lowering the pH of the menstrual fluid.

Others have incorporated monoesters and diesters of polyhydric aliphatic alcohols and a fatty acid containing from 8 to 18 carbon atoms. For example, glycerol monolaurate (GML) has been used to inhibit the production of S. aureus enterotoxins and TSST-1. However, as noted above, esterase is abundantly present in the vaginal epithelium and menstrual fluid. This esterase, in combination with esterase and lipase produced by bacteria can enzymatically degrade the esters into non-effective compounds. Until now, persons skilled in the art have not appreciated the affects of lipase and esterase on ester compounds. Thus, one or more ester compounds may have to be added to the absorbent article, such as a tampon pledget, in sufficiently high concentrations to detrimentally effect the normal flora present in the vaginal area. When the natural condition is altered, overgrowth by pathogen(s) may take place resulting in a condition known as vaginitis.

Accordingly, there exists a need for an absorbent product that has incorporated therein a compound that will: effectively inhibit the production of exoproteins, such as TSST-1, from Gram positive bacterium; will be substantially unaffected by the enzymes lipase and esterase; and will not substantially alter the natural flora found in the vaginal area.

SUMMARY OF THE INVENTION

Briefly, the present invention is based on the discovery that when one or more ether compounds having the general formula:

$$R_1O\text{---}R_2$$

wherein $R_1$ is a straight or branched alkyl or alkenyl group group having from 8 to 18 carbon atoms and $R_2$ is selected from an alcohol, a polyalkoxylated sulfate salt, or a polyalkoxylated sulfosuccinate salt are incorporated into an absorbent article, such as a catamenial tampon, the production of exoprotein in Gram positive bacterium is substantially inhibited.

It is a general object of the invention to provide an absorbent article which inhibits the production of exoproteins from Gram positive bacterium. A more specific object of the invention is to provide a catamenial tampon incorporating one or more ether compounds which act to substantially inhibit the production of TSST-1 and Enterotoxin B by S. aureus.

Another object of the invention is to provide a catamenial tampon that has incorporated therewith one or more compounds that will inhibit the production of exoproteins from Gram positive bacterium without significantly imbalancing the natural flora present in the vaginal tract.

Other objects and advantages of the present invention, and modifications thereof, will become apparent to persons skilled in the art without departure from the inventive concepts defined in the appended claims.

DETAILED DESCRIPTION OF THE PREFERRED EMBODIMENTS

This invention will be described in detail in connection with a catamenial tampon but would be understood by persons skilled in the art to be applicable to other disposable absorbent articles, such as: sanitary napkins, panty liners, adult incontinent undergarments, diapers, medical bandages and tampons such as those intended for medical, dental, surgical, and/or nasal use wherein inhibition of exoproteins from Gram positive bacteria would be beneficial.

Vaginal tampons suitable for use in this invention are usually made of absorbent fibers, including natural and synthetic fibers, compressed into a unitary body of a size which may easily be inserted into the vaginal cavity. They are normally made in an elongated cylindrical form in order that they may have a sufficiently large body of material to provide the required absorbing capacity, but may be made in a variety of shapes. The tampon may or may not be compressed, although compressed types are now generally preferred. The tampon may be made of various fiber blends including both absorbent and nonabsorbent fibers, which may or may not have a suitable cover or wrapper.

It has been found that certain ether compounds can substantially inhibit the production of exoprotein of Gram positive bacterium, more specifically, the production of TSST-1 and Enterotoxin B from S. aureus bacterium. The ether compounds of the present invention have the general formula:

$R_1—O—R_2$ wherein $R_1$ is a straight or branched alkyl or alkenyl group group having a chain of 8 to 18 carbon atoms and $R_2$ is selected from an alcohol, a polyalkoxylated sulfate salt or a polyalkoxylated sulfosuccinate salt.

The alkyl, or the $R_1$ moiety of the ether compounds useful herein, can be obtained from saturated and unsaturated fatty acid compounds. Suitable compounds include, $C_8$–$C_{18}$ fatty acids, and preferably, the fatty acids include, without limitation, caprylic, capric, lauric, myristic, palmitic and stearic acid whose carbon chain lengths are 8, 10, 12, 14, 16 and 18, respectively. Highly preferred materials include capric, lauric, and myristic.

Preferred unsaturated fatty acids are those having one or two cis-type double bonds and mixtures of these materials. Suitable materials include myrystoleic, palmitoleic, linolenic and mixtures thereof.

Desirably, the $R_2$ moiety is an aliphatic alcohol which can be ethoxylated or propoxylated for use in the ether compositions of the present invention. Suitable aliphatic alcohols include glycerol, sucrose, glucose sorbitol and sorbitan. Preferred ethoxylated and propoxylated alcohols include glycols such as ethylene glycol, propylene glycol, polyethylene glycol and polypropylene glycol.

The aliphatic alcohols can be ethoxylated or propoxylated by conventional ethoxylating or propoxylating compounds and techniques. The compounds are preferably selected from the group consisting of ethylene oxide, propylene oxide, and mixtures thereof, and similar ringed compounds which provide a material which is effective.

The $R_2$ moiety can further include polyalkoxylated sulfate and polyalkoxylated sulfosuccinate salts. The salts can have one or more cations. Preferably, the cations are sodium, potassium or both.

Preferred ether compounds of the present invention include laureth-3, laureth-4, laureth-5, PPG-5 lauryl ether, 1-0-dodecyl-rac-glycerol, sodium laureth sulfate, potassium laureth sulfate, disodium laureth (3) sulfosuccinate, dipotassium laureth (3) sulfosuccinate and polyethylene oxide (2) sorbitol ether.

In accordance with this invention, the tampon contains an effective amount of the inhibiting ether compound to substantially inhibit the formation of TSST-1 when the tampon is exposed to S. aureus bacteria. Effective amounts have been found to be at least about 0.005 millimoles of ether compound per gram of absorbent. Preferably, the ether compound ranges from about 0.005 millimoles per gram of absorbent to about 2 millimoles per gram of absorbent and more preferably 0.005 millimoles per gram of absorbent to about 0.2 millimoles per gram of absorbent. Although "compound" is used in the singular, one skilled in the art would understand that it includes the plural. That is, the absorbent article can include more than one ether compound.

The compositions of the present invention can be prepared and applied in any suitable form, but are preferably prepared in forms including, without limitation aqueous solutions, lotions, balms, gels, salves, ointments, boluses, suppositories, and the like.

The compositions may be applied to the absorbent article using conventional methods for applying an inhibitory agent to the desired absorbent article. For example, unitary tampons without separate wrappers, may be dipped directly into a liquid bath having the agent and then can be air dried, if necessary to remove any volatile solvents. For compressed tampons, impregnating of any of its elements is best done before compressing. The compositions when incorporated on and/or into the tampon materials may be fugitive, loosely adhered, bound, or any combination thereof. As used herein the term "fugitive" means that the composition is capable of migrating through the tampon materials.

It is not necessary to impregnate the entire absorbent body of the tampon with the inhibitory agent. Optimum results both economically and functionally, can be obtained by concentrating the material on or near the outer surface where it will be most effective during use.

The substantially inhibitory ether composition may additionally employ one or more conventional pharmaceutically-acceptable and compatible carrier materials useful for the desired application. The carrier can be capable of co-dissolving or suspending the materials used in the composition. Carrier materials suitable for use in the instant composition, therefore, include those well-known for use in the cosmetic and medical arts as a basis for ointments, lotions, creams, salves, aerosols, suppositories, gels and the like. A preferred carrier can be comprised of alcohols and surfactants.

The ether compositions of the present invention may additionally employ adjunct components conventionally found in pharmaceutical compositions in their art-established fashion and at their art-established levels. For example, the compositions may contain additional compatible pharmaceutically active materials for combination therapy, such as supplementary antimicrobials, anti-parasitic agents, antipruritics, astringents, local anaesthetics, or anti-inflammatory agents.

The invention will be illustrated by the following Examples, but the invention is not limited thereto and is fully applicable to the foregoing disclosure.

EXAMPLE A

The efficacy of the test compounds on TSST-1 production was determined by placing the desired concentration, expressed in millimoles/milliliter (millimolar hereinafter mM) of the active compound in 10 milliliters of a Growth Medium of each test compound in a Corning 50 ml conical polystyrene tube. The polystyrene tube is available from Scientific Products Division, Baxter Diagnostics Incorporated, 1430 Waukegan Road, McGaw Park, IL 60085-6787.

The Growth Medium was prepared as follows: Brain heart infusion broth (BHI), available from Becton Dickinson Microbiology Systems, Cockeysville, Md. 21030, was dissolved and sterilized according to the manufacturer's instructions. Ninety milliliters of BHI broth was supplemented with 10 ml fetal bovine serum (FBS), available from Sigma Chemical Company, P.O. Box 14508, St. Louis, Mo. 63178-9916. One milliliter of a 0.02 molar sterile solution of the hexahydrate of magnesium chloride, available from Sigma Chemical Company, was added to the BHI-FBS mixture. One milliliter of a 0.027 molar sterile solution of L-glutamine available from Sigma Chemical Company was also added to the BHI-FBS mixture.

If the test compound was not water soluble or water miscible, it was first dissolved at 50 times the desired concentration in 10 ml isopropanol, then diluted to the desired final concentration in 10 ml of the Growth Medium. Tubes of Growth Medium with an equivalent amount of isopropanol, but no test compound, were prepared as controls.

In preparation for inoculation of the tubes of Growth Medium containing the test compound, an inoculating broth was prepared as follows. S. aureus, (MNB) was streaked onto a sheep blood agar plate and incubated at 37° C. The test organism in this Example was obtained from Dr. Pat Schlievert, Department of Microbiology of the University of Minnesota Medical School, Minneapolis, Minn. After 24 hours of incubation three to five individual colonies were picked with a sterile inoculating loop and used to inoculate 10 ml of the Growth Medium. The tube of inoculated Growth Medium was capped with a S/P® diSPo® plug available from Scientific Products Division, Baxter Diagnostics, Incorporated and incubated at 37° C. in atmospheric air having 5% by volume $CO_2$. After 24 hours of incubation, the culture was removed from the incubator and mixed well on a S/P brand vortex mixer. A second tube containing 10 ml of the Growth Medium was inoculated with 0.5 ml of the above 24 hour culture and re-incubated at 37° C. in atmospheric air having 5% by volume $CO_2$. After 24 hours of incubation the culture was removed from the incubator and mixed well on a S/P brand vortex mixer. Each tube of Growth Medium containing a test compound and growth control tubes with or without isopropanol were inoculated with 0.1 ml of the prepared inoculating broth. The initial colony forming units (CFU) per ml of Growth Medium were approximately $1 \times 10^7$. The tubes were capped with S/P® diSPo® plugs and incubated at 37° C. in atmospheric air having 5% by volume $CO_2$. After 24 hours of incubation the tubes were removed from the incubator and the culture fluid was assayed for the number of colony forming units of S. aureus and prepared for analysis of TSST-1 per method described below.

The number of colony forming units per ml after incubation was determined by standard plate count procedure. The culture fluid broth was centrifuged and the supernatant subsequently filter sterilized through an Acrodisc® syringe filter unit available from Scientific Products Division, Baxter Diagnostics, Inc. The resulting fluid was frozen at −80° C. until assayed.

The amount of TSST-1 per milliliter was determined by a non-competitive, sandwich enzyme-linked immunoabsorbent assay (ELISA). Samples of the culture fluid and the TSST-1 reference standard were assayed in triplicate. The method employed was as follows: Four reagents, rabbit polyclonal anti-TSST-1 IgG (#LTI-101), rabbit polyclonal anti-TSST-1 IgG conjugated to horseradish peroxidase (#LTC-101), TSST-1 (#TT-606), and normal rabbit serum certified anti-TSST-1 free (#NRS-10) were purchased from Toxin Technology, Incorporated, 7165 Curtiss Avenue, Sarasota, Fla., 34231. Sixty-two microliters of polyclonal rabbit anti-TSST-1 IgG (#LTI-101) was appropriately diluted so that a 1:100 dilution gave an absorbance of 0.4 at 650 nanometers. This was added to 6.5 ml of 0.5 molar carbonate buffer, pH 9.6, and 100 microliters of this solution was pipetted into the inner wells of polystyrene microtiter plates #439454, obtained from Nunc-Denmark. The plates were covered and incubated overnight at 37° C. Unbound antitoxin was removed by three washes with phosphate buffered saline (pH 7.2) (0.011 molar $NaH_2PO_4$ and 0.9% [wt/vol] NaCl both available from Sigma Chemical Company) containing 0.5% [vol/vol] Tween 20 (PBS-Tween), also available from Sigma Chemical Company. The plates were treated with 100 microliters of a 1% [wt/vol] solution of bovine serum albumin (BSA), available from Sigma Chemical Company, covered, and incubated at 37° C. for one hour. Unbound BSA was removed by 6 washes with PBS-Tween. TSST-1 reference standard, serially diluted from 1–10 ng/ml in PBS-Tween, test samples treated with normal rabbit serum 10% [vol/vol] final concentration and reagent controls were pipetted in 100 microliter volumes to their respective wells. This was followed by incubation for two hours at 37° C. and three washes to remove unbound toxin. The rabbit polyclonal anti-TSST-1 IgG conjugated to horseradish peroxidase and diluted according to manufacturer's instructions was added (100 microliter volumes) to each microtiter well. The plates were covered and incubated at 37° C. for one hour.

Following incubation the plates were washed 6 times in PBS-Tween. Following this, the wells were treated with a solution consisting of 0.075 molar sodium citrate (pH 4.0), 0.6 millimolar 2,2'-Azino-bis-(3-ethylbenzthiazoline-6-sulfonic acid) diammonium salt and 0.009% [vol/vol] hydrogen peroxide, all available from Sigma Chemical Company. The intensity of the color reaction in each well was evaluated over time using a BioTek Model EL340 Microplate reader (OD 405 nm) and Kineticalc® software available from Biotek Instruments, Inc. TSST-1 concentrations in test samples were predicted from the reference toxin regression equations derived during each assay procedure. The efficacy of the compound in inhibiting the production of TSST-1 is shown in Table I below.

TABLE I

| Compound | mM Test Compound | CFU/ml | ELISA: TSST-1 ng/ml |
| --- | --- | --- | --- |
| Growth control | None | $3.3 \times 10^9$ | 381.8 |
| 1-O-dodecyl-rac-glycerol | 10.67 | $1.2 \times 10^9$ | 19.8 |
| Laureth-3 | 9.03 | $2.4 \times 10^8$ | 3.7 |
| Laureth-4 | 10.20 | $2.4 \times 10^8$ | 2.3 |
| Sodium laureth sulfate | 10.65 | $2.9 \times 10^3$ | ND |
| PPG-5 Laureth-5 | 7.35 | $2.0 \times 10^8$ | 1.6 |
| Disodium laureth sulfosuccinate | 9.84 | $3.4 \times 10^8$ | 2.3 |

ND = None detected

The above list of compounds (Commercial Name), their percent active compound, and vendor are as follows:
1-O-dodecyl-rac-glycerol, Sigma Chemical Company, 100%, P.O. Box 14508, St. Louis, MO 63178-9916.
Laureth-3, (Trycol 5966), 97%, Henkle Corporation, Emery Group, 4900 Este Avenue, Cincinnati, Ohio, 45232.
Laureth-4, (Trycol 5882), 100%, Henkle Corporation, 300 Brookside Avenue, Ambler, Pennsylvania 19002.
Sodium laureth sulfate, (Standapol ES-2), 25%, Henkle Corporation. PPG-5 Laureth-5, (Aethoxal B), 100%, Henkle Corporation.
Disodium laureth sulfosuccinate, (Standapul SH124-3), 39%, Henkle Corporation.

In accordance with the present invention, the data in Table 1 shows that S. aureus. MN8, when compared to the control, produced significantly less TSST-1 in the presence of the ether compounds. The ether compounds reduced the amount of exotoxin production ranging from about 95 percent to greater than 99.6 percent. However, although the amount of toxin produced was significantly reduced, in most cases the ether compounds did not substantially reduce the number of S. aureus cells.

EXAMPLE B

The efficacy of the test compounds in reducing the production of a second exoprotein of S. aureus was determined using S. aureus HOCH, a known producer of Enterotoxin B. The test organism in this Example was obtained from Dr. Pat Schlievert, Department of Microbiology of the University of Minnesota Medical School, Minneapolis, Minn. The experimental procedure for assessing the efficacy of the test compounds effect on growth of S. aureus HOCH and for production of a culture filtrate was the same as set forth in Example A above.

The amount of S. aureus enterotoxin B per milliliter was determined by Western Blot assay. Samples of the culture fluid and the Staphylococcal Enterotoxin B (SEB) reference standard were assayed in triplicate. The method employed was similar to that described in "A Rapid, Sensitive Method for Detection of Alkaline Phosphatase-Conjugated Anti-Antibody on Western Blots," M. S. Blake, K. H. Johnston, G. J. Russell-Jones and E. C. Gotschlich, *Analytical Biochemistry,* 136:175–179, 1984. The disclosure of which is incorporated herein by reference. Enterotoxin B was separated from other proteins in the test samples by sodium dodecyl sulfate-polyacrylamide gel (SDS-PAGE) electrophoresis. The upper stacking gel used 3% acrylamide gel, the lower separating gel contained 14% acrylamide gel. The upper gel was prepared with a comb containing twenty lanes spanning 15.5 centimeters of the top of the stacking gel. A low molecular weight SDS-PAGE standard, BioRad #161-0305 available from Bio-Rad Laboratories having offices at 2000 Alfred Nobel Drive, Hercules, Calif. 94547, SEB, #BT-202 from Toxin Technology, Incorporated, and culture extracts, as prepared above, were each mixed 1:1 with a loading buffer. The loading buffer contained 30% [vol/vol] glycerol, 15% [vol/vol] mercaptoethanol, 7% [wt/vol] sodium dodecyl sulfate, 0.0036% [wt/vol] bromphenol blue, and 0.76% [wt/vol] Trizma base with a pH of 6.8. The mixtures were boiled for 5 minutes, then twenty-five (25) microliters of each mixture was placed in a lane. The SDS-PAGE gel was electrophoresed (60 to 80 volts) for 90 minutes or until the dye front was through the stacking gel and for an additional 2.5 hours (160–170 volts) with an electrophoresis buffer of 0.61% [wt/vol] Tris base, 2.85% [wt/vol] glycine, 0.1% [wt/vol] SDS, pH 7.85. Proteins were transferred to a nitrocellulose transfer membrane, available from Schleicher and Schull, Inc., Keene, N.H. 03431, #BA 85, overnight approximately 15 hours at 200 milliamps in a Bio-Rad Trans-Blot® cell. The transfer buffer was composed of 0.3% [wt/vol] Tris base, 1.4% [wt/vol] glycine, 20% [vol/vol] methanol, pH 7.6.

The nitrocellulose membrane was treated for 45 minutes at 37° C. with 3% [wt/vol] gelatin in 0.02 molar Tris buffer, 0.5 molar NaCl, at pH 7.5 (TBS) to block non-specific reactions, then washed at 37° C. with TBS-0.05% [vol/vol] Tween 20 (TBS-Tween) for 45 minutes. The membrane was then submerged for 1.5 hours at 37° C. in 50 ml TBS-Tween containing 0.05 ml rabbit polyclonal anti-SEB IgG, #LBI-202 available from Toxin Technology, Incorporated.

The membrane was washed two times in TBS-Tween, then submerged a second time for 1.5 hours at 37° C. in a 50 ml solution of TBS-Tween with 25 microliters of goat anti-rabbit IgG conjugated to alkaline phosphatase. The membrane was washed twice in TBS-Tween and twice in TBS. The blot was developed with a reaction solution consisting of 2 mg 5-bromo-4-chloroindolyl phosphatase, 100 microliters of N,N dimethyl formamide, 18 ml 0.15 molar barbitol buffer, pH 9.2, 2 mg nitroblue tetrazolium, and 40 microliters of a 2 molar solution of $MgCl_2$ $6H_2O$, all available from Sigma. The reaction was stopped with a cold water wash. The amount of SEB produced in the presence of the test compound was estimated by a comparison with the staining intensity produced by a serial dilution of SEB. The efficacy of the test compound in inhibiting the production of Enterotoxin B is shown in Table II below.

TABLE II

| Compound | mM Test Compound | CFU/ml | Western Blot: SEB mg/ml |
|---|---|---|---|
| Growth control | None | $1.0 \times 10^9$ | 0.8 |
| 1-O-dodecyl-rac-glycerol | 10.67 | $7.0 \times 10^8$ | 0.8 |
| Laureth-3 | 9.03 | $8.3 \times 10^8$ | ND |
| Laureth-4 | 10.20 | $7.5 \times 10^8$ | ND |
| Sodium laureth sulfate | 2.13 | $1.2 \times 10^7$ | ND |
| PPG-5 Laureth-5 | 7.35 | $6.4 \times 10^8$ | ND |
| Disodium laureth sulfosuccinate | 9.84 | $2.1 \times 10^7$ | ND |

ND = None detected, <0.16 mg/ml

In accordance with the present invention, the data in Table II shows that S. aureus HOCH, when compared to the control, produced less SEB in the presence of the ether compounds. However, although the amount of toxin produced was substantially reduced, the ether compounds did not significantly reduce the number of S. aureus cells.

Another aspect of the invention is for a method of inhibiting the production of exoprotein from Gram positive bacteria in an absorbent product. In the method, the absorbent article, such as a tampon, is contacted with one or more of the above described ether compositions. The absorbent article has absorbed or coated on the fibers or cover material an effective amount of the composition so that the production of exoprotein from Gram positive bacteria is inhibited. Desirably, the production of TSST-1 and Enterotoxin B are inhibited.

While the invention has been described in conjunction with a specific embodiment, it is to be understood that many alternatives, modifications and variations will be apparent to those skilled in the art in light of foregoing description. Accordingly, this invention is intended to embrace all such alternatives, modifications and variations which fall within the spirit and scope of the appended claims.

I claim:

1. An absorbent article comprising an effective amount of an ether compound having the formula:

$R_1—O—R_2$ wherein $R_1$ is a straight or branched alkyl or alkenyl chain of 8 to 18 carbon atoms and $R_2$ is selected from the group consisting of an alcohol a polyalkoxylated sulfate salt and a polyalkoxylated sulfosuccinate salt wherein said compound is effective in substantially inhibiting the production of exoprotein from Gram positive bacteria.

2. The absorbent article of claim 1 wherein $R_1$ is alkyl.

3. The absorbent article of claim 1 wherein $R_1$ is alkenyl.

4. The absorbent article of claim 1 wherein said $R_1$ carbon chain is selected from the group consisting of caprylic, capdc, lauric, myristic, palmitic and stearic acid.

5. The absorbent article of claim 1 wherein said alcohol is an al iphatic alcohol.

6. The absorbent article of claim 5 wherein said aliphatic alcohol is selected from the group consisting of glycerol, glycol, sucrose, glucose, sorbitol and sorbitan.

7. The absorbent article of claim 6 wherein said glycol is selected from the group consisting of ethylene glycol, propylene glycol, polyethylene glycol, polypropylene glycol and combinations thereof.

8. The absorbent article of claim 1 wherein the cationic moiety of said sulfate salt and said sulfosuccinate salt are selected from the group consisting of sodium, potassium and combinations thereof.

9. The absorbent article of claim 1 wherein said compound is selected from the group consisting of laureth-3, laureth-4, laureth-5, PPG-5 lauryl ether, 1-0-dodecyl-rac-glycerol, sodium laureth sulfate, potassium laureth sulfate, disodium laureth (3) sulfosuccinate, dipotassium laureth (3) sulfosuccinate and polyethylene oxide (2) sorbitol ether.

10. The absorbent article of claim 1 wherein said compound is present in an amount greater than about 0.005 millimoles per gram of absorbent.

11. The absorbent article of claim 1 wherein said compound is present in an amount of about 0.005 millimoles per gram of absorbent to about 2 millimoles per gram of absorbent.

12. An absorbent article comprising an effective amount of an ether compound having the formula:

$R_1—O—R_2$ wherein $R_1$ is a straight or branched alkyl or alkenyl chain of 8 to 18 carbon atoms selected from the group consisting of caprylic, capric, lauric, myristic, palmitic and stearic acid and $R_2$ is selected from the group consisting of an alcohol, polyalkoxylated sulfate salt and polyalkoxylated sulfosuccinate salt, wherein said compound is effective in substantially inhibiting the production of exoprotein from Gram positive bacteria.

13. The absorbent article of claim 12 wherein $R_1$ is alkyl.

14. The absorbent article of claim 12 wherein $R_1$ is alkenyl.

15. The absorbent article of claim 12 wherein said alcohol is an aliphatic alcohol.

16. The absorbent article of claim 15 wherein said aliphatic alcohol is selected from the group consisting of glycerol, ethylene glycol, propylene glycol, polyethylene glycol, polypropylene glycol, sucrose, glucose, sorbitol and sorbitan.

17. The absorbent article of claim 12 wherein the cationic moiety of said sulfate salt and said sulfosuccinate salt are selected from the group consisting of sodium, potassium and combinations thereof.

18. The absorbent article of claim 12 wherein said compound is present in an amount greater than about 0.005 millimoles per gram of absorbent and said compound is selected from the group consisting of laureth-3, laureth-4, laureth-5, PPG-5 lauryl ether, 1-0-dodecyl-rac-glycerol, sodium laureth sulfate, potassium laureth sulfate, disodium laureth (3) sulfosuccinate, dipotassium laureth (3) sulfosuccinate, polyethylene oxide (2) sorbitol ether and combinations thereof.

19. An absorbent article comprising an effective amount of an ether compound having the formula:

$R_1—O—R_2$ wherein $R_1$ is selected from the group consisting of caprylic, capric, lauric, myristic, palmitic and stearic acid and $R_2$ is selected from the group consisting of an aliphatic alcohol, polyalkoxylated sulfate salt and polyalkoxylated sulfosuccinate salt, said aliphatic alcohol being selected from the group consisting of glycerol, ethylene glycol, propylene glycol, polyethylene glycol, polypropylene glycol, sucrose, glucose, sorbitol and sorbitan, said compound being effective in substantially inhibiting the production of TSST-1 and Enterotoxin B from *Staphylococcus aureus* bacteria.

20. The absorbent article of claim 19 wherein the cationic moiety of said sulfate salt and said sulfosuccinate salt are selected from the group consisting of sodium, potassium and combinations thereof.

21. The absorbent article of claim 19 wherein said compound is selected from the group consisting of laureth-3, laureth-4, laureth-5, PPG-5 lauryl ether, 1-0-dodecyl-rac-glycerol, sodium laureth sulfate, potassium laureth sulfate, disodium laureth (3) sulfosuccinate, dipotassium laureth (3) sulfosuccinate and polyethylene oxide (2) sorbitol ether.

22. A method for inhibiting the production of exoprotein from Gram positive bacteria in an absorbent product comprising contacting said absorbent product with an effective amount of an ether compound and exposing said absorbent product to one or more Gram positive bacteria, said ether compound having the formula:

$R_1—O—R_2$ wherein $R_1$ is a straight or branched alkyl or alkenyl chain of 8 to 18 carbon atoms and $R_2$ is selected from the group consisting of an alcohol, a polyalkoxylated sulfate salt and a polyalkoxylated sulfosuccinate salt.

23. The method of claim 22 wherein said ether compound is selected from the group consisting of laureth-3, laureth-4, laureth-5, PPG-5 lauryl ether, 1-0-dodecyl-rac-glycerol, sodium laureth sulfate, potassium laureth sulfate, disodium laureth (3) sulfosuccinate, dipotassium laureth (3) sulfosuccinate and polyethylene oxide (2) sorbitol ether.

24. The method of claim 22 wherein said absorbent product is a catamenial tampon.

* * * * *